US008463365B2

(12) United States Patent
Luiken

(10) Patent No.: US 8,463,365 B2
(45) Date of Patent: Jun. 11, 2013

(54) METHOD FOR IMAGING AND TREATING ORGANS AND TISSUES

(75) Inventor: George A. Luiken, San Diego, CA (US)

(73) Assignee: OncoFluor, Inc., Coronado, CA (US)

( * ) Notice: Subject to any disclaimer, the term of this patent is extended or adjusted under 35 U.S.C. 154(b) by 718 days.

(21) Appl. No.: 12/212,582

(22) Filed: Sep. 17, 2008

(65) Prior Publication Data

US 2009/0137909 A1    May 28, 2009

Related U.S. Application Data

(60) Provisional application No. 60/973,630, filed on Sep. 19, 2007.

(51) Int. Cl.
*A61B 6/00* (2006.01)
(52) U.S. Cl.
USPC .......................... 600/476; 600/310; 424/1.49
(58) Field of Classification Search
USPC ................. 600/310, 312, 317, 321, 329, 340, 600/407, 411, 431, 476; 424/1.49
See application file for complete search history.

(56) References Cited

U.S. PATENT DOCUMENTS

| | | | |
|---|---|---|---|
| 4,298,590 A * | 11/1981 | Bogoch | 424/1.49 |
| 4,444,744 A | 4/1984 | Goldenberg | |
| 4,569,789 A | 2/1986 | Blattler et al. | |
| 4,719,508 A | 1/1988 | Sasaki et al. | |
| 4,768,513 A | 9/1988 | Suzuki | |
| 4,786,813 A | 11/1988 | Svanberg et al. | |
| 4,821,117 A | 4/1989 | Sekiguchi | |
| 4,932,412 A | 6/1990 | Goldenberg | |
| 4,952,394 A | 8/1990 | Senter | |
| 5,088,492 A | 2/1992 | Takayama et al. | |
| 5,137,877 A | 8/1992 | Kaneko et al. | |
| 5,149,972 A | 9/1992 | Fay et al. | |
| 5,308,604 A | 5/1994 | Sinn et al. | |
| 5,349,066 A | 9/1994 | Kaneko et al. | |
| 5,398,685 A | 3/1995 | Wilk et al. | |
| 5,536,236 A | 7/1996 | Yabe et al. | |
| 5,618,528 A | 4/1997 | Cooper et al. | |
| 5,697,902 A | 12/1997 | Goldenberg | |
| 5,762,613 A | 6/1998 | Sutton et al. | |
| 5,773,292 A | 6/1998 | Bander | |
| 5,832,931 A * | 11/1998 | Wachter et al. | 128/898 |
| 5,843,401 A | 12/1998 | Dean et al. | |
| 5,871,711 A | 2/1999 | Dean et al. | |
| 6,083,485 A * | 7/2000 | Licha et al. | 424/9.6 |
| 6,110,106 A * | 8/2000 | MacKinnon et al. | 600/181 |
| 6,156,725 A | 12/2000 | Mukherjee et al. | |
| 6,241,672 B1 | 6/2001 | Hochman et al. | |
| 6,284,223 B1 | 9/2001 | Luiken | |
| 6,299,860 B1 | 10/2001 | Luiken | |
| 6,652,836 B2 * | 11/2003 | Luiken | 424/9.6 |
| 6,667,024 B1 | 12/2003 | Goldenberg et al. | |
| 7,011,812 B1 | 3/2006 | Griffiths et al. | |
| 2001/0055566 A1 * | 12/2001 | Luiken | 424/9.6 |
| 2005/0249667 A1 * | 11/2005 | Tuszynski et al. | 424/9.3 |
| 2007/0020278 A1 * | 1/2007 | Ross et al. | 424/155.1 |

FOREIGN PATENT DOCUMENTS

| | | |
|---|---|---|
| CA | 2223291 | 12/1996 |
| DE | 44 45 065.6 | 12/1994 |
| EP | 0 584 552 B1 | 3/1994 |
| WO | WO 96/17628 | 6/1996 |
| WO | WO 97/18841 | 5/1997 |
| WO | WO 98/47541 | 10/1998 |
| WO | WO 00/21576 | 4/2000 |

OTHER PUBLICATIONS

Cherry, W. B., "Evaluation of Commercial Fluorescein Isothiocyanates Used in Fluorescent Antibody Studies," *Stain Technology* 41(4):179-186 (1960).
Crean et al., "Evaluation of Porfimer Sodium Fluorescence for Measuring Tissue Transformation," Cancer 72(10):3068-3077 (1993).
D'Hallewin et al., "Fluorescence Detection of Flat Transitional Cell Carcinoma After Intravesical Instillation of Aminolevulinic Acid," *Am. J. Clin. Oncol.* 21(3):223-225 (1998).
Folli et al., "Immunophotodiagnosis of Colon Carcinomas in Patients Injected with Fluoresceinated Chimeric Antibodies Against Carcinoembryonic Antigen," *PNAS* 89:7973-7977 (1992).
Gutowski et al., "Intraoperative Immunophotodetection for Radical Resection of Cancers: Evaluation in an Experimental Model[1]," *Clinical Cancer Research* 7:1142-1148 (2001).
Hofland et al., "Internalization of [DOTA°, $^{125}$I-Tyr$^3$] Octreotide by Somatostatin Receptor-Positive Cells In Vitro and In Vivo: Implications for Somatostatin Receptor-Targeted Radioguided Surgery," *Proc. Assoc. Am. Physicians* III:63-69 (1999).
Keller et al., "Immunoscopy—a Technique Combining Endoscopy and Immunofluorescence for Diagnosis of Colorectal Carcinoma," *Gastrointestinal Endoscopy* 47(2):154-161 (1998).
Pèlegrin et al., "Antibody-Fluorescein Conjugates for Photoimmunodiagnosis of Human Colon Carcinoma in Nude Mice," *Cancer* 67(10): 2529-2537 (1991).
Riggs et al., "Isothiocyanate Compounds as Fluorescent Labeling Agents for Immune Serum," *American Journal Pathology* 34(6):1081-1097 (1958).
Virgoline, L., "Receptor Nuclear Medicine: Vasointestinal Peptide and Somatostatin Receptor Scintigraphy for Diagnosis and Treatment of Tumour Patients," *Eru J. Clin. Invest.* 27(10):793-800 (1997).
Wagner et al., "Principles of Nuclear Medicine," *W. B. Saunders Company* 2$^{nd}$ Ed. pp. 54-71, 178-184, and 1104-1117 (1995).

* cited by examiner

*Primary Examiner* — Unsu Jung
*Assistant Examiner* — Michael N Fisher
(74) *Attorney, Agent, or Firm* — Knobbe, Martens, Olson & Bear, LLP.

(57) ABSTRACT

The present invention provides methods and compositions for detecting and treating malignant tissue, organs or cells in a mammal. The method includes parenterally injecting a mammalian subject, at a locus or by a route providing access to the tissue or organ, with a composition including an antibody/fragment that is tagged with a fluorophore and a therapeutic isotope molecule, which specifically binds to the targeted organ, tissue or cell.

38 Claims, No Drawings

METHOD FOR IMAGING AND TREATING ORGANS AND TISSUES

CROSS REFERENCE TO RELATED APPLICATION

This application claims the benefit of priority under 35 U.S.C. §119(e) of U.S. Ser. No. 60/973,630, filed Sep. 19, 2007, the entire content of which is incorporated herein by reference.

BACKGROUND OF THE INVENTION

1. Field of the Invention

The present invention relates to methods for viewing the state of a body cavity or an internal organ of a mammalian body to allow more accurate removal of diseased tissue, and more particularly, to methods for detecting tumor tissue at an interior body site using a fluorescent targeting construct excited by light in the visible light range, and to treating such tissues.

2. Background Information

Many solid and liquid substances naturally emit fluorescent radiation when irradiated with ultraviolet light, visible, or near-infrared light. However, the radiation may fall within wide wavelength bands of low intensity. In the case of many natural objects, observations are partially obscured by natural fluorescence emanating simultaneously from many different compounds present in the sample under examination. In imaging devices such as microscopes, therefore, it is known to employ a filter for a selected wavelengths of light to screen out undesired fluorescence emanating from the object under observation.

In medical applications, a similar difficulty arises because both tumors and healthy tissue fluoresce naturally, albeit at different wavelengths. Consequently, when UV-activated fluorescence is used to detect tumors against a background of healthy tissue, identification of tumors is difficult. However, unlike most other cells of the body, tumor cells may possess a natural ability to concentrate and retain hematoporphyrin derivative dyes. Based upon this discovery, a technique was developed wherein a hematoporphyrin derivative fluorescent dye is administered and allowed to concentrate in a tumor to be examined to increase the fluorescence from the tumor as compared with that of healthy background tissue. Hematoporphyrin dyes fluoresce within a fluorescence spectrum between 610 and 700 nm, a spectrum easy to detect. However, the natural fluorescence from healthy in cells is still much more intense than that from the dyes, and has a broader fluorescence spectrum. Thus, the use of fluorescent dyes in diagnosis of tumors has not been wholly successful.

In endoscopic systems, it is also known to irradiate an internal organ with visible radiation to obtain a visible image and then to apply to the internal organ a fluorescent dye that concentrates in tumors over a period of time. The dye is allowed to concentrate, and then the internal organ is irradiated with excitation radiation for the dye to obtain a second fluorescent image. A body part having abnormal or diseased tissue, such as a cancer, may be identified by comparing an image produced by visible radiation of the internal organ with the image produced by fluorescence. To aid in visualizing the images received, endoscopic systems commonly utilize a television camera attached to a fiber optic scope having an optical guide fiber for guiding a beam from an external radiation source to the internal organ, and another optical guide fiber for transmitting a fluorescent image of the affected area to a television monitor for viewing. These two approaches are combined in a method of the type disclosed in U.S. Pat. No. 4,821,117, wherein a fluorescent dye is applied to an object to be inspected, is allowed to concentrate in the tumor, and the affected site is then alternately irradiated with visible light and with radiation at the excitation wavelength of the fluorophore. Images of the object obtained independently by visible and fluorescent light using a TV camera are stored in memory, and are simultaneously displayed in a television monitor to visually distinguish the affected area of the body part from the healthy background tissue.

In another type of procedure, such as is described in U.S. Pat. No. 4,786,813, a beam-splitting system splits the fluorescence radiation passing though the optical system into at least three parts, each of which forms a respective image of the object corresponding to each of the wavelength regions received. A detector produces a cumulative weighted signal for each image point corresponding to a single point on the object. From the weighted signal values of the various points on the object, an image of the object having improved contrast is produced. This technique is used to aid in distinguishing the fluorescence from the affected tissue from that produced by normal tissue.

A still more complex method of visualizing images from an endoscopic device uses a television scanning apparatus. For example, U.S. Pat. No. 4,719,508 discloses a method utilizing an endoscopic photographing apparatus wherein the endoscope includes an image sensor for successively generating image signals fed to a first frame memory for storing the image signals and a second frame memory for interlacing and storing image signals read successively from the first frame memory. The stored, interlaced image signals are delivered to a TV monitor for display to aid in visualizing the affected body part.

These prior art endoscopic systems, which rely on photographic processing of the image of the area of interest (i.e., via a TV monitor), while effective, have historically relied on increasingly complex and expensive equipment and substitute image processing to construct a diagnostic image (i.e., indirect viewing) for direct viewing of the affected body part without image processing, as by any type of camera or image processing device. A major shortfall of these prior art systems is that they all require specialized operator training and expertise, expensive, complex and technically sophisticated equipment, and are not generally available in community medical facilities. In addition, these prior art systems increase the time required to complete a surgical procedure, thereby adding to the patient's time under anesthesia, and subsequent risks therefrom. Finally, if the technology fails, there is no advantage over direct visualization.

Certain of the fluorescent dyes that concentrate in tumors due to natural bodily processes can be excited at wavelengths corresponding to those produced by lasers to accomplish diagnostic and therapeutic purposes. Consequently, lasers have also been used in procedures utilizing endoscopic systems in conjunction with fluorescent dyes to image and treat tumors. In one embodiment of this general method, a dye is used that absorbs laser light at two different wavelengths and/or laser powers, one that excites fluorescence without generating damaging heat in the tissue, and one that generates sufficient heat in the dye to destroy surrounding tissue. U.S. Pat. No. 4,768,513, for example, discloses a procedure in which a dye is applied to a body part suspected of containing a tumor, usually by local injection. The dye is allowed to concentrate in tumors and clear from healthy tissue over a period of days, and then the body part is irradiated with alternate pulses of two light sources: a white light of a known intensity and a fluorescence-exciting laser light. To compensate for variations in intensity of the fluorescence resulting from variations in the angle of incident light, and the like, visualization of the tumor is computer-enhanced by calculating the intensity of the fluorescence with respect to the known intensity of the white light. Ablation of a tumor detected using this method is accomplished by switching the laser to the heat-generating wavelength so as to destroy the cancerous tissue into which the fluorophore has collected.

While effective for diagnosing and treating tumors, such methods have two major drawbacks. Disease states other than tumors cannot be diagnosed, and laser visualization must be delayed for a period of two days or more after administration of the fluorescent dye to allow the dye to clear from normal tissue.

Monoclonal antibodies and other ligands specific for tumors have been developed for use in diagnosis of tumors, both in tissue samples and in vivo. In addition to such ligands, certain tumor-avid moieties are disproportionately taken up (and optionally or metabolized by tumor cells). Several well-known tumor-avid compounds are deoxyglucose, which plays a telling role in glycolysis in tumor cells; somatostatin, which binds to and/or is taken up by somatostatin receptors in tumor cells and particularly in endocrine tumors; and methionine, which is used as a substrate for metabolism in a wide array of tissues.

In such studies, deoxyglucose is used as a radio-tagged moiety, such as fluorodeoxyglucose ($^{18}$F-deoxyglucose), for detection of tumors of various types. It is believed that tumor cells experience such a mismatch between glucose consumption and glucose delivery that anaerobic glycolysis must be relied upon, thereby elevating the concentration of the radio-active tag in tumor tissue. It is also a possibility that the elevated concentration of deoxyglucose in malignant tumors may be caused by the presence of isoenzymes of hexokinase with abnormal affinities for native glucose or its analogs (A. Gjedde, Chapter 6: "Glucose Metabolism," Principles of Nuclear Medicine, 2nd Ed., W.B. Saunders Company, Philadelphia, Pa., pages 54-69). Similarly, due to the concentration of methionine and somatostatin in tumor tissue, radio-tagged methionine and somatostatin, and fragments or analogs thereof, are used in the art for non-invasive imaging of a variety of tumor types. One such procedure is known as somatostatin receptor scintigraphy (SRS).

Although these techniques have met with considerable success in determining the presence of tumor tissue, scintigraphic techniques are difficult to apply during a surgical procedure because of the equipment necessary for viewing the image provided by the radioisotope. Yet it is exactly at the time that the surgeon has made the incision or entered the body cavity that it would be most useful to "see" the outlines of the diseased tissue in real time and without the need for time-consuming, expensive image processing equipment. In addition, even using the best surgical techniques, it is well known that residual microscopic clusters of cells can and frequently are left behind after surgical excision of malignant tissue.

Thus, there is a need in the art for improved methods that can be used to directly visualize a broad range of putative disease sites without the need for use of image processing equipment as well as eliminate microscopic residual disease cells or clusters which are not visible to the naked eye, but which can lead to local or distant recurrence of a malignancy. Where real-time visualization is by means of endoscopic devices, direct visualization (as opposed to images created by image processing equipment) offers the additional advantage that the equipment required is comparatively simple to use and is less expensive than the equipment required to process images or create photographic displays from such images and no additional time is spent in image processing. In addition, there is a need in the art for a method of identifying diseased or abnormal tissue during surgical procedures so that immediate resection or biopsy of the identified tissue can be performed while the surgeon "sees" the outlines of the diseased or abnormal tissue. Finally, the ability to destroy any residual microscopic disease by linking a therapeutic radio-isotope to the fluorescence-tagged tumor-specific construct would offer the chance to improve cure rates for a wide variety of malignancies.

SUMMARY OF THE INVENTION

The present invention overcomes many of these problems in the art by providing method(s) for in vivo identification of diseased tissue in a subject in need thereof. As such, the present invention relates to methods for visually detecting tumor tissue at an interior or exterior body site using tumor-specific fluorescent targeting constructs, which are excited by light in the visible range (i.e. 350-500 nm), to allow more accurate removal of all diseased tissue, and for treating residual microscopic or macroscopic tumor tissue with therapeutic radio-isotopes attached to the tumor-specific fluorescent targeting constructs.

The invention method includes illuminating an in vivo body part of the subject containing diseased tissue with light having at least one excitation wavelength in the range from about 350 nm to about 510 nm, about 401 nm to about 510 nm, or about 470 nm to about 500 nm. Fluorescence emanating from a fluorescent targeting construct administered to the subject and which has specifically bound to and/or been taken up by the diseased tissue in the body part, in response to the at least one excitation wavelength is directly viewed to determine the location and/or surface area of the diseased tissue in the subject.

In one embodiment, the fluorescent targeting construct comprises a fluorophore-tagged antibody or fluorophore-tagged tumor avid moiety and a therapeutic isotope molecule. The fluorophore-tagged antibody or fluorophore-tagged tumor avid moiety is responsive to the excitation wavelength administered to the subject. In another embodiment, the therapeutic isotope is an electron emitter and a positron (+) beta emitter, and allows for the destruction of microscopic clusters of diseased cells to prevent local or distant recurrence of a malignancy.

In another embodiment, the present invention provides methods for utilizing a diagnostic procedure during surgery in a subject in need thereof. In this embodiment of the invention diagnostic methods, an in vivo body part (e.g., tissue or organ) of the subject containing diseased tissue is illuminated with light having at least one excitation wavelength in the range from about 350 nm to about 510 nm, about 401 nm to about 510 nm, or about 470 nm to about 500 nm. A targeting construct preadministered to the subject that fluoresces in response to the at least one excitation wavelength and which has specifically bound to and/or been taken up by the diseased tissue or organ in the body part is directly viewed to determine the location and/or surface area of the diseased tissue in the subject is determined from the directly viewed fluorescence from the targeting construct and all or at least a portion of the diseased tissue is removed. After excision of all visible malignant tissue (aided by induced tumor fluorescence), clusters of microscopic cancer cells (minimal residual disease) will be eliminated by beta-emitting radioisotopes). The targeting construct comprises a fluorophore-tagged antibody or fluorophore-tagged tumor avid moiety and a therapeutic isotope molecule.

In yet another embodiment, the present invention provides methods for in vivo diagnosis of tumor tissue in a subject in need thereof. In this embodiment, the invention method includes contacting samples of tumor cells obtained from the subject in vitro with a plurality of detectably labeled compounds, each of which binds to or is selectively taken up by a distinct tumor type to determine which of the compounds is bound to or taken up by the sample tumor cells. A biologically compatible fluorescing targeting construct is fabricated to contain a compound determined by this process that is tagged with a therapeutic isotope molecule to bind to and/or be taken up by the sample tumor cells and which fluoresces in response to light having at least one excitation wavelength in the range from about 350 nm to about 510 nm, about 401 nm to about 510 nm, or about 470 nm to about 500 nm. The location and/or surface area of the tumor tissue in the in vivo body part is diagnosed by administering a diagnostically effective amount of the targeting construct to the subject, allowing the targeting construct to bind to or be taken up by in vivo tumor cells, and directly viewing fluorescence emanating from the targeting construct bound to or taken up in the tumor tissue in response to illumination of the tumor tissue with a light that provides the required excitation wavelength.

As such, the present invention also provides use of a fluorophore-tagged tumor-specific antibody or a fluorophore-tagged tumor avid moiety, and a therapeutic isotope molecule, which is capable of specifically binding and/or being taken up by diseased tissues in a body part in the manufacture of a composition for the in vivo diagnosis, visualization, or therapy of residual diseased tissue in a subject in need thereof. The in vivo body part of the subject containing diseased tissue is irradiated with light having at least one excitation wavelength in the range from about 350 nm to about 510 nm, about 401 nm to about 510 nm, or about 470 nm to about 500 nm, and the fluorescence emitted in response to the light from the fluorophore-tagged tumor-specific antibody or a fluorophore-tagged tumor avid moiety, which has specifically bound to and/or taken up by the diseased tissue in the body part is directly viewed, and the location and/or surface area of the diseased tissue in the subject from the fluorescence provided by the targeting construct is determined.

In certain embodiments, the methods of the present invention include a positron emission tomography (PET) scan that is performed prior to surgery to identify tumor masses having the fluorescent targeting construct attached thereto, thereby providing information on the location of the diseased tissue in the body cavity or organ.

In another embodiment, the present invention provides a means of eliminating microscopically small clusters of malignant cells that are not visible to the naked eye or with standard magnification devices by means of the therapeutic isotope molecule within the fluorescent targeting construct. The therapeutic isotope is an electron emitter and a positron (+) beta emitter, and allows for the elimination of microscopic clusters of diseased cells to prevent local or distant recurrence of a malignancy.

As such, the present invention also provides use of a fluorophore-tagged tumor-specific antibody or a fluorophore-tagged tumor avid moiety, and a therapeutic isotope molecule, which is capable of specifically binding and/or being taken up by diseased tissues in a body part in the manufacture of a composition for the elimination of microscopically small clusters of malignant cells that are not visible to the naked eye or with standard magnification devices. The therapeutic isotope is an electron emitter and a positron (+) beta emitter, and allows for the elimination of microscopic clusters of diseased cells to prevent local or distant recurrence of a malignancy.

DETAILED DESCRIPTION OF THE INVENTION

The present invention provides methods for in vivo identification, diagnosis, and therapy of diseased tissue in a subject in need thereof. The invention method includes illuminating an in vivo body part of the subject containing diseased tissue with light having at least one excitation wavelength in the range from about 350 nm to about 510 nm, about 401 nm to about 510 nm, or about 470 nm to about 500 nm. Fluorescence emanating from a fluorescent targeting construct administered to the subject and which has specifically bound to and/or been taken up by the diseased tissue in the body part, in response to the at least one excitation wavelength is directly viewed to determine the location and/or surface area of the diseased tissue in the subject. See U.S. Pat. Nos. 4,444,744, 4,932,412, 5,697,902 and 7,011,812, the entire contents of which are incorporated herein by reference, for additional information regarding use of a radioisotope for therapy when attached to an antibody.

Light having a wavelength range from 401 nm to 510 nm lies within the visible range of the spectrum, in contrast to UV light, which lies within the non-visible range from about 4 nm to about 400 nm. As such, the excitation light used in practice of the invention diagnostic methods will contain at least one wavelength of light that illuminates surrounding tissue as well as excites fluorescence from the fluorescent targeting construct used in practice of the invention methods. The excitation light may be monochromatic or polychromatic. To compensate for the tendency of such background effect to obscure the desired visualization, a filter may be used to screen out wavelengths above about 510 nm in the excitation light, thereby eliminating wavelengths that would be reflected from healthy tissue so as to cause loss of resolution of the fluorescent image. Alternatively, it is possible view the diagnostic site through a filter that substantially screens out wavelengths other than the peak emission wavelength of the fluorophore used. For example, if the fluorescent targeting construct emits fluorescence at a known peak emission wavelength of 520 nm, the filter can be selected to substantially eliminate wavelengths of light below about 520 nm. Use of a filter in the practice of the invention diagnostic methods is expressly intended to be encompassed by the term "directly viewing" as applied to the invention diagnostic methods.

Use of one or more filters to screen out wavelengths of light in a selected wavelength band or screen out all wavelengths except those in a narrow band is well known in the art and will encompass the use of such simple devices as filtering eyeglasses worn by the diagnostician or physician, and/or filtered viewing lenses for endoscopic devices that are used during the diagnostic procedure.

Operating rooms can be equipped with an overhead light that emits wavelengths of light in the optical spectrum useful in practice of invention diagnostic methods, such as a Blue LED. Such a light can be utilized in the practice of the invention diagnostic methods merely by turning out the other lights in the operating room (to eliminate extraneous light that would be visibly reflected from tissue in the body part under investigation) and shining the excitation light into the body cavity or surgically created opening so that the fluorescent image received directly by the eye of the observer (e.g., the surgeon) is predominantly the fluorescent image emanating from the fluorophore(s) in the field of vision. Light emanating from a source in the 401-510 nm range could be filtered to aid in accomplishing the goal of direct visualization by the observer so that light reflecting from the body part, other than that from the fluorescing moiet(ies), is minimized or eliminated.

Light in the 350 nm to 510 nm, 401 nm to 510 nm, or 470 nm to 500 nm wavelength range is readily absorbed in tissue. Accordingly, in the invention diagnostic methods, the diseased tissue (and bound or taken-up targeting construct) is "exposed" to the excitation light (e.g., by surgically created opening or endoscopic delivery of the light to an interior location. The invention method is particularly suited to in vivo detection of diseased tissue located at an interior site in the subject, such as within a natural body cavity or a surgically created opening, where the diseased tissue is "in plain view" (i.e., exposed to the human eye) to facilitate a procedure of biopsy or surgical excision, but would be equally applicable to visualizing malignant tissue of the skin or appendages. As the precise location and/or surface area of the tumor tissue are readily determined by the invention diagnostic procedure, the invention method is a valuable guide to the surgeon, who needs to "see" in real time the exact outlines, size, etc., of the mass to be resected as the surgery proceeds. Once the diseased tissue is removed, any microscopic clusters of cells, with the radio-labeled tumor-specific construct attached, would be destroyed by the therapeutic isotope molecule contained within the fluorescent targeting construct.

If the putative diseased site is a natural body cavity or surgically produced interior site, an endoscopic device can be used to deliver the excitation light to the site, to receive fluorescence emanating from the site within a body cavity, and to aid in formation of a direct image of the fluorescence from the diseased tissue. For example, a lens in the endoscopic device can be used to focus on the detected fluorescence as an aid in visualizing the diseased tissue. As used herein, such endoscope-delivered fluorescence is said to be "directly viewed" by the practitioner and the tissue or organ to which the targeting construct binds or in which it is taken up must be "in plain view" to the endoscope since the light used in the invention diagnostic procedure will not contain wavelengths of light that penetrate tissue, such as wavelengths in the near infrared range. Alternatively, as described above, the excitation light may be directed by any convenient means, such as a hand-held LED or fixed light source, into a body cavity or surgical opening containing a targeting construct administered as described herein and the fluorescent image so produced can be directly visualized by the eye of the observer without aid from an endoscope. With or without aid from any type of endoscopic device, the fluorescence produced by the invention method is such that it can be viewed without aid of an image processing device, such as a CCD camera, TV monitor, photon collecting device, and the like.

In one embodiment of the invention diagnostic methods, diseased or abnormal tissues or organs are contemporaneously viewed through a surgical opening to facilitate a procedure of biopsy or surgical excision. As the location and/or surface area of the diseased tissue or organ are readily determined by the invention diagnostic procedure, the invention method is a valuable guide to the surgeon, who needs to know the exact outlines, size, etc., of the mass, for example, for resection as the surgery proceeds.

Accordingly, in this embodiment, the present invention provides methods for utilizing a diagnostic procedure during surgery in a subject in need thereof by irradiating an in vivo body part of the subject containing diseased tissue with light having at least one excitation wavelength in the range from about 350 nm to about 510 nm, about 401 nm to about 510 nm, or about 470 nm to about 500 nm, directly viewing fluorescence emanating from a targeting construct administered to the subject that has specifically bound to and/or been taken up by the diseased tissue in the body part, wherein the targeting construct fluoresces in response to the at least one excitation wavelength, determining the location and/or surface area of the diseased tissue in the subject, and removing at least a portion of the tumor tissue.

In another embodiment, the methods further provide for performing a positron emission tomography (PET) scan prior to surgery to identify tumor masses having the fluorescent targeting construct attached thereto. Such pre-surgery scans will provide the user (e.g., surgeon) with additional information on the location of the diseased tissue in the body cavity or organ.

In yet another embodiment, the present invention provides methods for in vivo diagnosis of tumor tissue in a subject in need thereof. In this embodiment, the invention method comprises contacting samples of tumor cells obtained from the subject in vitro with a plurality of detectably labeled compounds, each of which binds to or is selectively taken up by a distinct tumor type, determining which of the compounds is bound to or taken up by the sample tumor cells, administering a diagnostically effective amount of at least one biologically compatible fluorescing targeting construct containing a compound determined to bind to and/or be taken up by the sample tumor cells that is tagged with a therapeutic isotope molecule and a fluorophore responsive to at least one, wavelength of light in the range from about 350 nm to about 510 nm, about 401 nm to about 510 nm, or about 470 nm to about 500 nm, and diagnosing the location and/or surface area of the tumor tissue in the in vivo body part by directly viewing fluorescence emanating from the targeting construct bound or taken up in the tumor tissue upon irradiation thereof with light providing the at least one excitation wavelength for the fluorescent targeting construct.

As used herein, the terms "sample" and "biological sample" refer to any sample suitable for the methods provided by the present invention. In one embodiment, the biological sample of the present invention is a tissue sample, e.g., a biopsy specimen such as samples from needle biopsy. In other embodiments, the biological sample of the present invention is a sample of bodily fluid, e.g., serum, plasma, urine, and ejaculate.

In one embodiment of the invention method, a single type of fluorescent moiety is relied upon for generating fluorescence emanating from the irradiated body part (i.e., from the fluorescent targeting construct that binds to or is taken up by diseased tissue). Since certain types of healthy tissue fluoresce naturally, in such a case it is important to select a fluorescent moiety for the targeting construct that has a predominant excitation wavelength that does not contain sufficient wavelengths in the visible range of light to make visible the surrounding healthy tissue and thus inhibit resolution of the diseased tissue. Therefore, the light source used in practice of this embodiment of the invention emits light in the range from about 350 nm to about 510 nm, about 401 nm to about 510 nm, or about 470 nm to about 500 nm. Thus, the methods of the invention involve contact of diseased tissue with a fluorescent targeting construct.

Exemplary fluorescent targeting constructs include anti-tumor antigen antibodies (e.g., FAB fragment, bispecific antibodies, diabodies, or antibody fragments) or tumor avid compounds and a biologically compatible fluorescing moiety. As used herein, the terms "fluorophore-tagged antibody" and "fluorophore-tagged tumor avid compound" respectively refer to such fluorescent targeting constructs that are responsive to specific excitation wavelengths administered to a subject in need of the methods of the invention.

In another embodiment, the fluorescent targeting construct is additionally tagged with a therapeutic isotope molecule that is both an electron emitter and a positron (+) "beta" emitter. See U.S. Pat. No. 6,667,024, the entire content of which is incorporated herein by reference, for additional information regarding use of alpha or beta emitters for therapeutic use. The advantage of including a therapeutic isotope molecule is that when attached to the fluorophore-tagged antibody or the fluorophore-tagged tumor avid compound, the therapeutic isotope molecule provides the dual roles of (i) allowing for pre-surgery external imaging with a positron emission tomography (PET) scanner of the subject to provide additional information and/or a guide for the operating surgeon in accurately determining the location of the tumor or diseased tissue, and (ii) providing post-surgery "clean-up" of any microscopic clusters of diseased tissue or cells that are too small to be seen by the surgeon, but could be a source of local and/or distant recurrences of the disease/cancer. The dual emitter therapeutic isotopes provide the added benefit of having short half-lives, thereby providing minimal risk of radiation exposure to the surgeon during the procedure. Exemplary therapeutic isotopes include, but are not limited to, those shown in Table 1 below:

TABLE 1

| Therapeutic Isotope | Half Life |
| --- | --- |
| Astatine-211 | 7 h |
| Bismuth-213 | 46 min |
| Carbon-11 | 20.38 min |
| Chromium-51 | 28 d |
| Cobalt-57 | 272 d |
| Cobalt-60 | 10.5 months |
| Copper-64 | 13 h |
| Dysprosium-165 | 2 h |
| Erbium-169 | 9.4 d |
| Fluorine-18 | 1.8 h |
| Gallium-67 | 78 h |
| Holmium-166 | 26 h |
| Indium-111 | 2.8 d |
| Iodine-123 | 13 h |
| Iodine-125 | 60 d |
| Iodine-131 | 8 d |
| Iridium-192 | 74 d |
| Iron-59 | 46 d |
| Krypton-81m | 13 sec |
| Lutetium-177 | 6.7 d |
| Molybdenum-99 | 66 h |
| Nitrogen-13 | 10 min |
| Oxygen-15 | 2 min |
| Palladium-103 | 17 d |
| Phosphorus-32 | 14 d |
| Potassium-42 | 12 h |
| Rhenium-186 | 3.8 d |
| Rhenium-188 | 17 h |
| Rubidium-81 | 4.6 h |
| Rubidium-82 | 65 h |
| Samarium-153 | 47 h |
| Selenium-75 | 120 d |
| Sodium-24 | 15 h |
| Strontium-89 | 50 d |
| Strontium-92 | 25 d |
| Thallium-201 | 73 h |
| Technetium-99m | 6 h |
| Terbium-149 | 4.3 min |
| Xenon-133 | 5 d |
| Ytterbium-169 | 32 d |
| Ytterbium-177 | 1.9 h |
| Yttrium-90 | 64 h |

PET is a more precise and sophisticated technique using isotopes produced in a cyclotron. A positron-emitting radionuclide is introduced into a subject, usually by injection, and accumulates in the target tissue. As it decays it emits a positron, which promptly combines with a nearby electron resulting in the simultaneous emission of two identifiable gamma rays in opposite directions. These emissions are detected by a PET camera and give a very precise indication of their origin.

In alternative embodiments, the invention methods may additionally comprise the step of administering to the subject one or more supplemental fluorescing targeting constructs (e.g., antibodies, or biologically active fragments thereof, having attached fluorophores) that bind to the initial fluorescent targeting construct and/or to each other to enhance the fluorescence emanating from the target tissue. For instance, a fluorescently-tagged anti-fluorophore antibody may be administered to bind to any previously administered fluorescently-tagged antibody or tumor-avid molecule. The purpose of the supplemental fluorescing targeting construct is to increase the intensity of fluorescence from the targeting ligand of the first administered targeting construct and thereby to aid in detection of diseased or abnormal tissue in the body part.

It is generally good practice to allow the targeting construct to bind to and/or be taken up by any targeting tissue that may be present at the site under investigation and then, before administration of the supplemental fluorescing targeting construct(s), to substantially remove (e.g., wash) from the body part any unbound targeting construct to maximize the opportunity for fluorescence from the supplemental fluorescing targeting constructs(s) to aid in detecting the presence of any target tissue present in the body part. Usually, the supplemental fluorescing targeting constructs are successively administered to build up the fluorescent signal from the target tissue. For example, if the fluorescent targeting construct comprises a humanized IgG monoclonal antibody specific for a breast cancer antigen, the next-administered fluorescing targeting construct may comprise an anti-fluorophore antibody, such as anti-fluorescein, and the third-administered fluorescing targeting construct may comprise an anti-idiotype antibody. Those of skill in the art will be able to devise combinations of successively administered fluorescing targeting constructs, each of which specifically binds to the targeting construct or to one or more of the earlier administered supplemental fluorescing targeting constructs. It is presently preferred that all of the fluorescing targeting constructs used to identify the target tissue comprise fluorophores that fluoresce within the same wavelength band or at the same wave length as does the initially administered targeting construct (e.g. a fluorescing sensitive to the invention wavelength of light in the initially administered targeting construct) to minimize the number of different light sources that need to be employed to excite simultaneous fluorescence from all of the different targeting constructs used in practice of the invention method.

In yet another embodiment, the invention method further comprises the step of administering to the subject at least one supplemental fluorescent targeting construct (e.g., comprising an antibody, or a biologically active fragment thereof having an attached fluorophore) that specifically binds to or is taken up by normal tissue or constructs in the body part, wherein fluorescence from the supplemental fluorescent targeting construct(s) in response to the irradiating light is a different color (i.e., has a different wavelength) than that from the florescent targeting construct that is selected to bind to or be taken up by the target tissue. The difference in the colors of the fluorescence emanating from fluorophores in targeting constructs targeted to normal and to diseased or abnormal target tissue aids the observer in determining the location and size of the target tissue. Use of supplemental fluorophores provides the advantage that any natural fluorescence emanating from normal tissue is obscured by the fluorescence emanating from fluorophore(s) in supplemental targeting constructs targeted to the normal tissue in the body part. The greater the difference in color between the fluorescence emanating from normal and target tissue, the easier it is for the observer to visualize the outlines and size of the target tissue. For instance, targeting a fluorescing targeting construct comprising a fluorophore producing red light to the target tissue (i.e., abnormal tissue) and a fluorophore producing green light to healthy tissue aids the observer in distinguishing the target tissue from the normal tissue. Those of skill in the art can readily select a combination of fluorophores that present a distinct visual color contrast.

The spectrum of light used in the practice of the invention method is selected to contain at least one wavelength that corresponds to the predominant excitation wavelength of the targeting construct, or of a biologically compatible fluorescing moiety (e.g., fluorophore-tagged antibody or fluorophore-tagged tumor avid compound) contained within the targeting construct. Generally the excitation light used in practice of the invention method comprises at least one excitation wavelength of light in the wavelength range from about 350 nm to about 510 nm, about 401 nm to about 510 nm, or about 470 nm to about 500 nm.

However, when a combination of targeting ligands that fluoresce at different wavelengths is used in practice of the invention, the spectrum of the excitation light must be broad enough to provide at least one excitation wavelength for each of the fluorophores used. For example, it is particularly important when fluorophores of different colors are selected to distinguish normal from diseased tissue, that the excitation spectrum of the light(s) include excitation wavelengths for the fluorophores targeted to normal and target tissue.

The fluorescing moiety of the targeting construct or of the supplemental fluorescing targeting ligand(s) can be any chemical or protein moiety that is biologically compatible (e.g., suitable for in vivo administration) and which fluoresces in response to excitation light as described herein. Since the targeting ligand is administered to living tissue, biological compatibility includes the lack of substantial toxic effect to the individual in general if administered systemically, or to the target tissue, if administered locally, at the dosage administered. Non limiting examples of fluorophores that can be used in the practice of the invention include fluorescein, mithramycin, Oregon green, and cascade blue, and the like, and combinations of any two or more thereof.

Additional non-limiting examples of fluorescent compounds that fluoresce in response to an excitation wavelength in the range from 350 nm to about 510 nm, about 401 nm to about 510 nm, or about 470 nm to about 500 nm are found in Table 2 below:

TABLE 2

| COMPOUND | EXCITATION RANGE (nm) | EMISSION RANGE (nm) |
| --- | --- | --- |
| Acridine Red | 455-600 | 560-680 |
| Acridine Yellow | 470 | 550 |
| Acriflavin | 436 | 520 |
| AFA (Acriflavin Feulgen SITSA) | 355-425 | 460 |
| Alexa Fluor 488 | 470-490 | 520 |
| ACMA | 430 | 474 |
| Astrazon Orange R | 470 | 540 |
| Astrazon Yellow 7 GLL | 450 | 480 |
| Atabrine | 436 | 490 |

TABLE 2-continued

| COMPOUND | EXCITATION RANGE (nm) | EMISSION RANGE (nm) |
| --- | --- | --- |
| Auramine | 460 | 550 |
| Aurophosphine | 450-490 | 515 |
| Aurophosphine G | 450 | 580 |
| Berberine Sulphate | 430 | 550 |
| BOBO-1, BO-PRO-1 | 462 | 481 |
| BOPRO1 | 462 | 481 |
| Brilliant Sulpho-flavin FF | 430 | 520 |
| Calcein | 494 | 517 |
| Calcofluor White | 440 | 500-520 |
| Cascade Blue | 400 | 425 |
| Catecholamine | 410 | 470 |
| Chinacrine | 450-490 | 515 |
| Coriphosphine O | 460 | 575 |
| DiA | 456 | 590 |
| Di-8-ANEPPS | 488 | 605 |
| DiO [DiOC$_{18}$(3)] | 484 | 501 |
| Diphenyl Brilliant Flavine 7GFF | 430 | 520 |
| Euchrysin | 430 | 540 |
| Fluorescein | 494 | 518 |
| Fluorescein Iso-thiocyanate (FITC) | 490 | 525 |
| Fluo 3 | 485 | 503 |
| FM1-43 | 479 | 598 |
| Fura Red | 472 (low[$Ca^{2+}$]) 436 (high[$Ca^{2+}$]) | 657 (low[$Ca^{2+}$]) 637 (high[$Ca^{2+}$]) |
| Genacryl Brilliant Yellow 10GF | 430 | 485 |
| Genacryl Pink 3G | 470 | 583 |
| Genacryl Yellow SGF | 430 | 475 |
| Gloxalic Acid | 405 | 460 |
| 3-Hydroxypyrene-5,-8,10-TriSulfonic Acid | 403 | 513 |
| 7-Hydroxy-4-methylcourmarin | 360 | 455 |
| 5-Hydroxy-Tryptamine (5-HT) | 380-415 | 520-530 |
| Lucifer Yellow CH | 425 | 528 |
| Lucifer Yellow VS | 430 | 535 |
| LysoSensor Green DND-153, DND-189 | 442 | 505 |
| Maxilon Brilliant Flavin 10 GFF | 450 | 495 |
| Maxilon Brilliant Flavin 8 GFF | 460 | 495 |
| Mitotracker Green FM | 490 | 516 |
| Mithramycin | 450 | 570 |
| NBD | 465 | 535 |
| NBD Amine | 450 | 530 |
| Nitrobenzoxadidole | 460-470 | 510-650 |
| Nylosan Brilliant Flavin E8G | 460 | 510 |
| Oregon Green 488 fluorophore | 496 | 524 |
| Phosphine 3R | 465 | 565 |
| Quinacrine Mustard | 423 | 503 |
| Rhodamine 110 | 496 | 520 |
| Rhodamine 5 GLD | 470 | 565 |
| Rhodol Green fluorophore | 499 | 525 |
| Sevron Orange | 440 | 530 |
| Sevron Yellow L | 430 | 490 |
| SITS (Primuline) | 395-425 | 450 |
| Sulpho Rhodamine G Extra | 470 | 570 |
| SYTO Green fluorescent nucleic acid stains | 494 ± 6 | 515 ± 7 |
| Thioflavin S | 430 | 550 |
| Thioflavin 5 | 430 | 550 |
| Thiozol Oragne | 453 | 480 |
| Uranine B | 420 | 520 |
| YOYO-1, YOYO-PRO-1 | 491 | 509 |

Since the fluorescence properties of biologically compatible fluorophores are well known, or can be readily determined by those of skill in the art, the skilled practitioner can readily select a useful fluorophore or useful combination of fluorophores, and match the wavelength(s) of the excitation light to the fluorophore(s). The toxicity of fluorescein is minimal as it has been used safely in vivo in humans for many years, but the toxicity of additional useful fluorophores can be determined using animal studies known in the art.

Preferably, the targeting construct (e.g., the ligand moiety of the invention targeting construct) is selected to bind to and/or be taken up specifically by the target tissue of interest, for example to an antigen or other surface feature contained on or within a cell that characterizes a disease or abnormal state in the target tissue. As in other diagnostic assays, it is desirable for the targeting construct to bind to or be taken up by the target tissue selectively or to an antigen associated with the disease or abnormal state; however, targeting constructs containing ligand moieties that also bind to or are taken up by healthy tissue or cell structures can be used in the practice of the invention method so long as the concentration of the antigen in the target tissue or the affinity of the targeting construct for the target tissue is sufficiently greater than for healthy tissue in the field of vision so that a fluorescent image representing the target tissue can be clearly visualized as distinct from any fluorescence coming from healthy tissue or structures in the field of vision. For example, colon cancer is often characterized by the presence of carcinoembryonic antigen (CEA), yet this antigen is also associated with certain tissues in healthy individuals. However, the concentration of CEA in cancerous colon tissue is often greater than is found in healthy tissue, so an anti-CEA antibody could be used as a ligand moiety in the practice of the invention. In another example, deoxyglucose is taken up and utilized by healthy tissue to varying degrees, yet its metabolism in healthy tissues, except for certain known organs, such as the heart, is substantially lower than in tumor. The known pattern of deoxyglucose consumption in the body can therefore be used to aid in determination of those areas wherein unexpectedly high uptake of deoxyglucose signals the presence of tumor cells.

Thus, in one embodiment, the disease or abnormal state detected by the invention method can be any type characterized by the presence of a known target tissue for which a specific binding ligand is known. For example, various heart conditions are characterized by production of necrotic or ischemic tissue or production of artherosclerotic tissue for which specific binding ligands are known. As another illustrative example, breast cancer is characterized by the production of cancerous tissue identified by monoclonal antibodies to CA15-3, CA19-9, CEA, or HER2/neu. It is contemplated that the target tissue may be characterized by cells that produce either a surface antigen for which a binding ligand is known, or an intracellular marker (i.e. antigen), since many targeting constructs penetrate the cell membrane. Representative disease states that can be identified using the invention method include such various conditions as different types of tumors, bacterial, fungal and viral infections, and the like. As used herein "abnormal tissue" includes precancerous conditions, cancer, necrotic or ischemic tissue, and tissue associated with connective tissue diseases, and auto-immune disorders, and the like.

The term "cancer" as used herein, includes any malignant tumor including, but not limited to, carcinoma, sarcoma and lymphoma. Cancer arises from the uncontrolled and/or abnormal division of cells that then invade and destroy the surrounding tissues. As used herein, "proliferating" and "proliferation" refer to cells undergoing mitosis. As used herein, "metastasis" refers to the distant spread of a malignant tumor from its sight of origin. Cancer cells may metastasize through the bloodstream, through the lymphatic system, across body cavities, or any combination thereof. Examples of the types of target tissue suitable for diagnosis or examination using the invention method include cancer of breast, lung, colon, prostate, pancreas, skin, stomach, small intestine, testicle, head and neck, thyroid, gall bladder, brain, endocrine tissue, and the like, as well as combinations of any two or more thereof.

Representative examples of antigens for some common malignancies and the body locations in which they are commonly found are shown in Table 3 below. Targeting ligands, such as antibodies, for these antigens are known in the art.

TABLE 3

| ANTIGEN | TUMORS WHERE COMMONLY FOUND |
| --- | --- |
| CEA (carcinoembryonic antigen) | colon, breast, lung, pancreas |
| PSA (prostate specific antigen) | prostate cancer |
| PSMA (prostate specific membrane antigen) | prostate cancer |
| CA-125 | ovarian cancer, breast, colon, lung |
| CA 15-3 | breast cancer, lung, colon, pancreas, medullary cancer of the thyroid, prostate |
| CA 19-9 | breast cancer |
| HER2/neu | breast cancer |
| α-feto protein | testicular cancer, hepatic cancer |
| β-HCG | testicular cancer, choriocarcinoma (human chorionic gonadotropin) |
| MUC-1 | breast cancer, colon, lung, |
| MUC-2 | colorectal cancer, colon, lung |
| TAG 72 | breast cancer, colon cancer, and pancreatic cancer |
| Estrogen receptor | breast cancer, uterine cancer |
| Progesterone receptor | breast cancer, uterine cancer |
| AR (androgen receptor) | prostate cancer |
| EGFr (epidermal growth factor receptor) | bladder cancer |
| IGFr (insulin like growth factor) | Sarcoma |

In one embodiment of the invention method, the ligand moiety of the targeting construct is a protein or polypeptide, such as an antibody, or biologically active fragment thereof, preferably a monoclonal antibody. The supplemental fluorescing targeting construct(s) used in practice of the invention method may also be or comprise polyclonal or monoclonal antibodies tagged with a fluorophore. The term "antibody" as used in this invention includes intact molecules as well as functional fragments thereof, such as Fab, F(ab')$_2$, and Fv that are capable of binding the epitopic determinant. These functional antibody fragments retain some ability to selectively bind with their respective antigen or receptor and are defined as follows:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule that can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of making these fragments are known in the art. (See for example, Harlow & Lane, Antibodies: A Laboratory Manual, Cold Spring Harbor Laboratory, New York, 1988, incorporated herein by reference). As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibody fragments of the present invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated in their entireties by reference. See also Nisonhoff et al., *Arch. Biochem. Biophys.* 89:230, 1960; Porter, *Biochem. J.* 73:119, 1959; Edelman et al., *Methods in Enzymology, Vol.* 1, page 422 Academic Press, 1967; and Coligan et al. at sections 2.8.1-2.8.10 and 2.10.1-2.10.4. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of $V_H$ and $V_L$ chains. This association may be noncovalent, as described in Inbar et al., *Proc. Nat'l Acad. Sci. USA* 69:2659, 1972. Alternatively, the variable chains can be linked by an intermolecular disulfide bond or cross-linked by chemicals such as glutaraldehyde. See, e.g., Sandhu, supra. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., Methods: a Companion to Methods in Enzymology, 2: 97, 1991; Bird et al., *Science* 242:423-426, 1988; Pack et al., *Bio/Technology* 11:1271-77, 1993; Sandhu, supra, and Ladner et al., U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., Methods: a Companion to Methods in Enzymology, 2: 106, 1991.

Antibodies which bind to a tumor cell can be prepared using an intact polypeptide or biologically functional fragment containing small peptides of interest as the immunizing antigen. The polypeptide or a peptide used to immunize an animal (derived, for example, from translated cDNA or chemical synthesis) can be conjugated to a carrier protein, if desired. Commonly used carriers that are chemically coupled to the peptide include keyhole limpet hemocyanin (KLH), thyroglobulin, bovine serum albumin (BSA), and tetanus toxoid, and the like. The coupled peptide is then used to immunize the animal (e.g., a mouse, a rat, or a rabbit).

The preparation of such monoclonal antibodies is conventional. See, for example, Kohler & Milstein, *Nature* 256:495, 1975; Coligan et al., sections 2.5.1-2.6.7; and Harlow et al., in: Antibodies: a Laboratory Manual, page 726 (Cold Spring Harbor Pub., 1988), which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, for example, Coligan et al., sections 2.7.1-2.7.12 and sections 2.9.1-2.9.3; Barnes et al., Purification of Immunoglobulin G (IgG), in: Methods in Molecular Biology, Vol. 10, pages 79-104 (Humana Press, 1992).

Antibodies of the present invention may also be derived from subhuman primate antibodies. General techniques for raising therapeutically useful antibodies in baboons can be found, for example, in Goldenberg et al., International Patent Publication WO 91/11465 (1991) and Losman et al., 1990, *Int. J. Cancer* 46:310, which are hereby incorporated by reference. Alternatively, a therapeutically useful antibody may be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86:3833, 1989, which is hereby incorporated in its entirety by reference. Techniques for producing humanized monoclonal antibodies are described, for example, by Jones et al., *Nature* 321:522, 1986; Riechmann et al., *Nature* 332:323, 1988; Verhoeyen et al., *Science* 239: 1534, 1988; Carter et al., *Proc. Nat'l Acad. Sci. USA* 89:4285, 1992; Sandhu, *Crit. Rev. Biotech.* 12:437, 1992; and Singer et al., *J. Immunol.* 150:2844, 1993, which are hereby incorporated by reference.

It is also possible to use anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

In a presently preferred embodiment of the invention method, the ligand moiety in the fluorescent targeting construct used in practice of the invention can be selected from among the many biologically compatible tumor-avid moieties that bind with specificity to receptors and/or are preferentially taken up by tumor cells, and can be used as the ligand moiety in the invention targeting constructs. Tumor-avid moieties that are preferentially "taken up" by tumor cells may enter the cells through surface or nuclear receptors (e.g., hormone receptors), pores, hydrophilic "windows" in the cell lipid bilayer, and the like.

Illustrative of this class of tumor-avid moieties are somatostatin, somatostatin receptor-binding peptides, deoxyglucose, methionine, histidine, and the like. Particularly useful somatostatin receptor-binding peptides are a long-acting, octapeptide analog of somatostatin, known as octreotide (D-phenylalanyl-L-cysteinyl-L-phenylalanyl-D-tryptophyl-L-lysyl-L-threonyl-N-[2-hydroxy-1-(hydroxymethyl)propyl]-L-cysteinamide cyclic (2.fwdarw.7)-disulfide), lanreotide, an oral formulation of octreotide, P829, P587, and the like. Somatostatin-binding peptides are disclosed in U.S. Pat. No. 5,871,711, and methods for linking such peptides covalently to a radioisotope through their carboxyl terminal amino acid under reducing conditions are disclosed in U.S. Pat. No. 5,843,401, which are both incorporated herein by reference in their entireties. One of skill in the art can readily adapt such teachings for the preparation of fluorescence-sensitive somatostatin receptor-binding peptides by substituting the fluorescing moieties of this invention in the place of a radioisotope.

Somatostatin and somatostatin receptor-binding peptides are particularly effective for use as the tumor-avid moiety in the targeting construct in the invention diagnostic procedures when the disease state is a neuroendocrine or endocrine tumor. Examples of neuroendocrine tumors that can be diagnosed using the invention method include adenomas (GH-producing and TSH-producing), islet cell tumors, carcinoids, undifferentiated neuroendocrine carcinomas, small cell and non small cell lung cancer, neuroendocrine and/or intermediate cell carcinomas, neuroendocrine tumors of ovary, cervix, endometrium, breast, kidney, larynx, paranasal sinuses, and salivary glands, meningiomas, well differentiated glia-derived tumors, pheochromocytomas, neuroblastomas, ganglioneuro(blasto)mas, paragangliomas, papillary, follicular and medullary carcinomas in thyroid cells, Merkel cell carcinomas, and melanomas, as well as granulomas and lymphomas. These tumor cells are known to have somatostatin receptors and can be targeted using somatostatin or somatostatin receptor binding peptides as the tumor-avid moiety in the invention fluorescent targeting construct.

Vasointestinal peptide (VIP), which is used in VIP receptor scintigraphy (I. Virgolini, *Eur J. Clin. Invest.* 27(10):793-800, 1997, is also useful in the invention method for diagnosis of small primary adenocarcinomas, liver metastases and certain endocrine tumors of the gastrointestinal tract.

Another molecule illustrative of the tumor-avid moieties that are preferentially taken up by tumors is deoxyglucose, which is known to be preferentially taken up in a variety of different types of tumors. Illustrative of the types of tumors that can be detected using deoxyglucose as the tumor-avid ligand moiety in the fluorescent targeting construct as disclosed herein include Preferred tumor targets for deoxyglucose include melanoma, colorectal and pancreatic tumors, lymphoma (both HD and NHL), head and neck tumors, myeloma, cancers of ovary, cancer, breast, and brain (high grade and pituitary adenomas), sarcomas (grade dependent), hepatoma, testicular cancer, thyroid (grade dependent) small cell lung cancer, bladder and uterine cancer, and the like.

Yet other tumor-avid compounds that can be used as the targeting ligand in an invention fluorescing targeting construct are 1-amino-cyclobutane-1-carboxylic acid and L-methionine. L-methionine is an essential amino acid that is necessary for protein synthesis. It is known that malignant cells have altered methionine metabolism and require an external source of methionine.

Additional examples of biologically compatible tumor-avid compounds that bind with specificity to tumor receptors and/or are preferentially taken up by tumor cells include mammalian hormones, particularly sex hormones, neurotransmitters, and compounds expressed by tumor cells to communicate with each other that are preferentially taken up by tumor cells, such as novel secreted protein constructs arising from chromosomal aberrations, such as transfers or inversions within the clone.

The term "hormone" is used herein to refer to compounds that are expressed within a mammal for action at a remote location and includes such compounds as sex hormones, cell growth hormones, cytokines, endocrine hormones, erythropoietin, and the like. As is known in the art, a number of tumor types express receptors for hormones, for example, estrogen, progesterone, androgens, such as testosterone, and the like. Such hormones are preferentially taken up by tumor cells, for example, via specific receptors. It is also known in the art that the particular type of receptors expressed by a tumor cell may change over time with the same cell or cell mass, for example, expressing estrogen receptors at one point in time and with the estrogen receptors being substantially replaced with androgen receptors at another point in time.

Therefore, in another embodiment according to the present invention, the invention diagnostic method comprises pre-screening of target tumor cells to determine which receptors are currently being expressed by the target cells. In this embodiment, the invention diagnostic method comprises contacting sample(s) of tumor cells obtained from a subject in vitro with a plurality of detectably labeled tumor-avid compounds, and determining which of the tumor-avid compounds bind to or are taken up by the sample cells. The invention diagnostic method further comprises administering to the subject a diagnostically effective amount of one or more biologically compatible fluorescing targeting constructs, each comprising as ligand moiety at least one of the tumor-avid compounds determined to bind to and/or be taken up by the tumor cells so as to allow the fluorescing targeting construct to bind to and/or be taken up selectively in vivo by tumor tissue, irradiating an in vivo body part of the subject suspected of containing the tumor tissue with light having at least one wavelength in the excitation spectrum of the targeting construct under conditions that substantially eliminate extraneous light to the in vivo body part, and directly viewing fluorescence emanating from the fluorescing targeting construct bound to or taken up by the tumor tissue so as to determine the location and/or surface area of the tumor tissue in the in vivo body part. Of course, if the tests determine that the tumor cells are concurrently taking up more than one tumor-avid compound in substantial proportion (e.g., both estrogen and progesterone), the more than one tumor avid compound so determined can be used as the tumor-avid ligand moieties in the targeting constructs in the invention diagnostic method.

Methods for obtaining test tumor cells for prescreening to determine the type(s) of tumor-avid compounds that are currently being taken up (e.g., by specific receptors expressed by the tumor cells) are well known in the art. For example, such techniques as fine needle aspirates, brush biopsies, core needle biopsies, pleural effusion, ascetic fluid urine and sputum cytology, bone marrow biopsy and aspirates, scrapings, excisional biopsies, and the like, can in many instances be utilized to obtain test tumor cells relatively non-invasively.

In vitro tests useful for determining the tumor-avid compounds that are being taken up by test tumor cells are numerous and also well known in the art. Such in vitro tests generally involve either sequentially or simultaneously contacting the test cells with a plurality of different tumor-avid compounds. For example, the test cells can be contacted with a panel or library of detectably labeled hormones and/or other known tumor-avid compounds to determine which of the detectably labeled compounds bind to and/or are taken up by the test cells.

In the practice of the present invention, the fluorescent moiety sensitive to an excitation wavelength in the range of about 350 nm to about 510 nm, about 401 nm to about 510 nm, or about 470 nm to about 500 nm, can be linked to the tumor-avid compound used as the ligand moiety in the targeting construct by any method presently known in the art for attaching two moieties, so long as the attachment of the linker moiety to the ligand moiety does not substantially impede binding of the targeting construct to the target tissue and/or uptake by the tumor cells, for example, to a receptor on a cell. Those of skill in the art will know how to select a ligand/linker pair that meets this requirement. For example, with regard to octreotide, it has been shown that coupling of a linker to Tyr3 or Phe1 of octreotide does not prevent the internalization of octreotide after binding to the somatostatin receptor (L. J. Hofland et al., *Proc. Assoc. Am. Physicians* 111:63-9, 1999). It is also known that 1-amino-cyclobutane-1-carboxylic acid can be tagged at the 3 carbon of the ring.

The length of the optional linker moiety is chosen to optimize the kinetics and specificity of ligand binding, including any conformational changes induced by binding of the ligand moiety to a target, such as an antigen or receptor. The linker moiety should be long enough and flexible enough to allow the ligand moiety and the target to freely interact and not so short as to cause steric hindrance between the proteinaceous ligand moiety and the target.

In one embodiment, the linker moiety is a heterobifunctional cleavable cross-linker, such as N-succinimidyl (4-iodoacetyl)-aminobenzoate; sulfosuccinimidyl(4-iodoacetyl)-aminobenzoate; 4-succinimidyl-oxycarbonyl-α-(2-pyridyldithio) toluene; sulfosuccinimidyl-6-[α-methyl-α-(pyridyldithiol)-toluamido]hexanoate; N-succinimidyl-3-(-2-pytidyldithio)-proprionate; succinimidyl-6-[3(-(-2-pyridyldithio)-proprionamido]hexanoate; sulfosuccinimidyl-6-[3(-(-2-pyridyldithio)-propionamido]hexanoate; 3-(2-pyridyldithio)-propionyl hydrazide, Ellman's reagent, dichlorotriazinic acid, S-(2-thiopyridyl)-L-cysteine, and the like. Further bifunctional linking compounds are disclosed in U.S. Pat. Nos. 5,349,066, 5,618, 528, 4,569,789, 4,952,394, and 5,137,877, each of which is incorporated herein by reference in its entirety.

These chemical linkers can be attached to purified ligands using numerous protocols known in the art, such as those described in Pierce Chemicals "Solutions, Cross-linking of Proteins: Basic Concepts and Strategies," Seminar #12, Rockford, Ill.

In another embodiment presently preferred, the linker moiety is a peptide having from about 2 to about 60 amino acid residues, for example from about 5 to about 40, or from about 10 to about 30 amino acid residues. This alternative is particularly advantageous when the ligand moiety is proteinaceous. For example, the linker moiety can be a flexible spacer amino acid sequence, such as those known in single-chain antibody research. Examples of such known linker moieties include GGGGS (SEQ ID NO: 1), $(GGGGS)_{1-12}$ (SEQ ID NO: 2), GKSSGSGSESKS (SEQ ID NO: 3), GSTSGSGKSSEGKG (SEQ ID NO: 4), GSTSGSGKSSEGSGSTKG (SEQ ID NO: 5), GSTSGSGKSSEGKG (SEQ ID NO: 6), GSTSGSGKPGSGEGSTKG (SEQ ID NO: 7), EGKSSGSGSESKEF (SEQ ID NO: 8), SRSSG (SEQ. ID NO: 9), SGSSC (SEQ ID NO: 10), and the like. A Diphtheria toxin trypsin sensitive linker having the sequence AMGRSGGGCAG-NRVGSSLSCGGLNLQAM (SEQ ID NO: 11) is also useful. Alternatively, the peptide linker moiety can be VM or AM, or have the structure described by the formula: $AM(G_2\ to\ 4S)_X$ QAM wherein Q is selected from any amino acid and X is an integer from 1 to 11 (SEQ ID NO:12). Additional linking moieties are described, for example, in Huston et al., *PNAS* 85:5879-5883, 1988; Whitlow, M., et al., *Protein Engineering* 6:989-995, 1993; Newton et al., *Biochemistry* 35:545-553, 1996; A. J. Cumber et al., *Bioconj. Chem.* 3:397-401, 1992; Ladurner et al., *J. Mol. Biol.* 273:330-337, 1997; and U.S. Pat. No. 4,894,443, the latter of which is incorporated herein by reference in its entirety.

The targeting constructs and supplemental targeting constructs used in practice of the invention method can be administered by any route known to those of skill in the art. As used herein, the term "administration" or "administering" is defined to include an act of providing a compound or pharmaceutical composition of the invention to a subject in performing the methods of the invention. Exemplary routes of administration include, but are not limited to, intravenously, intraarticularly, intracisternally, intraocularly, intraventricularly, intrathecally, intramuscularly, intraperitoneally, intradermally, intracavitarily, and the like, as well as combinations of any two or more thereof.

The most suitable route for administration will be intravenously, but may vary depending upon the disease state to be treated, or the location of the suspected condition or tumor to be diagnosed.

The targeting construct is administered in a "diagnostically effective amount." As used herein, a "diagnostically effective amount" refers to the quantity of a targeting construct necessary to aid in direct visualization of any target tissue located in the body part under investigation in a subject. As used herein, the term "subject" refers to any mammal, such as a domesticated pet, farm animal, or zoo animal, but preferably is a human. Amounts effective for diagnostic use will, of course, depend on the size and location of the body part to be investigated, the affinity of the targeting construct for the target tissue, the type of target tissue, as well as the route of administration.

Since individual subjects may present a wide variation in severity of symptoms and each targeting construct has its unique diagnostic characteristics, including, affinity of the targeting construct for the target, rate of clearance of the targeting construct by bodily processes, the properties of the fluorophore contained therein, and the like, the skilled practitioner will weigh the factors and vary the dosages accordingly.

The invention composition can also be formulated as a sterile injectable suspension according to known methods using suitable dispersing or wetting agents and suspending agents. The sterile injectable preparation may also be a sterile injectable solution or suspension in a non-toxic parenterally-acceptable diluent or solvent, for example, as a solution in 1-4 butanediol. Sterile, fixed oils are conventionally employed as a solvent or suspending medium. For this purpose any bland fixed oil may be employed, including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate, or the like. Buffers, preservatives, antioxidants, and the like, can be incorporated as required, or, alternatively, can comprise the formulation.

The invention fluorescing targeting constructs can be produced by well known techniques. For example, well known techniques of protein synthesis can be used to obtain proteinaceous components of the targeting construct if the amino acid sequence of the component is known, or the sequence can first be determined by well known methods, if necessary. Some of the ligand genes are now commercially available. An advantage of obtaining commercially available genes is that they have generally been optimized for expression in *E. coli*. A polynucleotide encoding a protein, peptide or polynucleotide of interest, can be produced using DNA synthesis technology. Methods for obtaining the DNA encoding an unavailable gene and expressing a gene product therefrom are well known and will not be described here in detail.

A fluorescent targeting construct comprising a proteinaceous ligand moiety, a proteinaceous linker moiety, and a proteinaceous fluorophore can also be produced as a fusion protein using well known techniques wherein a host cell is transfected with an expression vector containing expression control sequences operably linked to a nucleic acid sequence coding for the expression of the fusion protein (Molecular Cloning A Laboratory Manual, Sambrook et al., eds., 2nd Ed., Cold Spring Harbor Laboratory, N.Y., 1989).

As used herein, the terms "peptide" and "polypeptide" refer to a polymer in which the monomers are amino acid residues which are joined together through amide bonds, alternatively referred to as a polypeptide. When the amino acids are alpha-amino acids, either the L-optical isomer or the D-optical isomer can be used, the L-isomers being preferred. Additionally, unnatural amino acids such as beta-alanine, phenylglycine, and homoarginine are meant to be included. Commonly encountered amino acids that are not gene-encoded can also be used in the present invention, although preferred amino acids are those that are encodable. For a general review, see, for example, Spatola, A. F., in Chemistry and Biochemistry of Amino Acids, Peptides and Proteins, B. Weinstein, ed., Marcel Dekker, New York, p. 267, 1983.

Although the invention has been described with reference to the above example, it will be understood that modifications and variations are encompassed within the spirit and scope of the invention. Accordingly, the invention is limited only by the following claims.

What is claimed is:

1. A method for the treatment of diseased tissue in a subject in need thereof comprising:
   (a) illuminating an in vivo exposed body cavity, integument, or organ of a subject containing diseased tissue with light having at least one excitation wavelength in the range from 350 nm to 510 nm;
   (b) directly viewing fluorescence emanating from a fluorescent targeting construct bound to diseased tissue in the illuminated body cavity, integument, or organ, the construct comprising:
   a fluorophore-tagged tumor-specific antibody and a therapeutic isotope molecule; or
   a fluorophore-tagged tumor avid moiety and a therapeutic isotope molecule, wherein the fluorophore-tagged tumor-specific antibody or fluorophore-tagged tumor avid moiety is responsive to the excitation wavelength administered to the subject and has specifically bound to or been taken up by the diseased tissue in the exposed body cavity, integument, or organ;
   (c) identifying diseased tissue in the subject by direct visualization of the fluorescence provided by the fluorescent targeting construct without the aid of a capture device;
   (d) removing diseased tissue identified by the direct visualization; and
   (e) allowing the therapeutic isotope molecule to remain in contact with residual diseased tissue not removed in step (d).

2. The method of claim 1, wherein the fluorophore-tagged tumor-specific antibody is an anti-tumor antigen antibody, an Fab fragment, or a bispecific antibody.

3. The method of claim 1, wherein the therapeutic isotope molecule is an electron emitter and a positron (+) beta emitter.

4. The method of claim 3, wherein the therapeutic isotope molecule is Samarium-153, Rhenium-188, or Copper-64.

5. The method of claim 1, wherein the therapeutic isotope molecule allows for external imaging with a positron emission tomography (PET) scan device.

6. The method of claim 1, wherein the light has at least one excitation wavelength in the range of 401 nm to 510 nm or 470 nm to 510 nm.

7. The method of claim 1, wherein the tumor-avid moiety is a hormone, a hormone receptor-binding peptide, deoxyglucose, somatostatin, a somatostatin receptor-binding peptide, or a combination of any two or more thereof.

8. The method of claim 7, wherein the hormone receptor-binding peptide is HER2 neu, an estrogen receptor, a progesterone receptor, an androgen receptor, a TSH receptor, or a calcium sensing receptor.

9. The method of claim 7, wherein the tumor-avid moiety is chromaggranin, somatostatin or a somatostatin receptor-binding peptide.

10. The method of claim 7, wherein the diseased tissue is a neuroendocrine or endocrine tumor.

11. The method of claim 10, wherein the diseased tissue is from a cancer selected from the group consisting of thyroid cancer, parathyroid adenoma, adrenal cancer, islet cell cancer, and pituitary adenoma.

12. The method of claim 10, wherein the diseased tissue is from a cancer selected from the group consisting of melanoma, insulinoma, head and neck cancer, hepatic cancer, breast cancer, pancreatic cancer, small cell and non-small cell lung cancer, ovarian, endometrial, or fallopian tube cancer, pituitary or adrenal cancer, brain tumor, esophageal, gastric, small bowel or colorectal cancer, anal cancer, basal cell cancer, squamous cell cancer of the skin, epithelial cancer, carcinoid tumor, prostate cancer, bladder cancer, vulvar and testicular germ cell tumor, breast cancer, Ewing's sarcoma, soft tissue sarcoma, or and osteosarcoma.

13. The method of claim 7, wherein the somatostatin receptor-binding peptide is octreotide, lanreotide, P587 or P829.

14. The method of claim 1, wherein the tumor-avid moiety is deoxyglucose.

15. The method of claim 14, wherein diseased tissue is a brain tumor, esophageal cancer, gastric cancer, small bowel cancer, pancreatic cancer, hepatic cancer, colorectal cancer, malignant melanoma, basal cell cancer, squamous cell cancer of the skin, epithelial tumor, lung cancer, testicular germ cell tumor, breast cancer, soft tissue sarcoma, Ewing's sarcoma, or osteosarcoma.

16. The method of claim 1, wherein the tumor-avid moiety is 1-amino-cyclobutane-1-carboxylic acid, methionine, a methionine derivative, or histidine.

17. The method of claim 1, wherein the light is monochromatic, and wherein the excitation wavelength of the light is matched to an excitation wavelength of the fluorescent targeting construct.

18. The method of claim 17, wherein the excitation wavelength is 400-510 nm, and wherein the fluorescent targeting construct comprises fluorescein.

19. The method of claim 1, wherein the exposed body cavity is a natural body cavity.

20. The method of claim 1, wherein the exposed organ contains a muscle tumor, bone tumor, malignant mole, a thyroid mass, a brain tumor, a testicular cancer, or a prostate cancer.

21. The method of claim 1, wherein the exposed body cavity is made surgically.

22. The method of claim 1, wherein a source of the light is located outside of the body of the subject.

23. The method of claim 1, wherein the diseased tissue is associated with a condition selected from the group consisting of tumors, pre-cancerous conditions, necrotic conditions, and ischemic conditions.

24. The method of claim 1, further comprising administering to the subject a supplemental fluorescent targeting construct that associates with normal tissue in the in vivo exposed body cavity, integument, or organ, wherein fluorescence from the supplemental fluorescent targeting construct in response to the excitation light is a different color than fluorescence from the fluorescent targeting construct, and wherein the different color distinguishes the diseased tissue from the normal tissue.

25. The method of claim 1, wherein the fluorescing fluorescent targeting construct further comprises a linker moiety that attaches the tumor-specific antibody or the tumor avid moiety to the fluorescent targeting construct.

26. The method of claim 25, wherein the tumor-avid moiety is a hormone, deoxyglucose, somatostatin, a somatostatin receptor-binding peptide, methionine, a methionine derivative, histidine, or a combination of any two or more thereof.

27. The method of claim 1, wherein the fluorescent targeting construct is administered by a route selected from the group consisting of intravenously, intramuscularly, intraarticularly, intracisternally, intraocularly, intraventricularly, intrathecally, intercavitarily, intraperitoneally, intradermally, and a combination of any two or more thereof.

28. The method of claim 1, wherein the fluorescent targeting construct is administered by local injection.

29. The method of claim 1, wherein the fluorescent targeting construct is administered systemically.

30. A method for the treatment of tumor tissue in a subject in need thereof comprising:
(a) contacting samples of tumor cells obtained from the subject in vitro with a plurality of detectably labeled compounds, each of which binds to one or more cell-surface tumor antigen or is selectively taken up by the tumor cells;
(b) determining which of the compounds is bound to the one or more cell-surface tumor antigen or taken up by the tumor cells;
(c) administering to the subject a diagnostically effective amount of at least one biologically compatible fluorescent targeting construct containing a compound determined in step (b) that is tagged with a therapeutic isotope molecule to bind to or be taken up by exposed tumor tissue or organ that matches the sample tumor cells, wherein the fluorescent targeting construct fluoresces in response to light having at least one excitation wavelength in the range from 350 nm to 510 nm; and
(d) identifying tumor tissue in the in vivo body cavity or organ by directly viewing the fluorescence provided by the fluorescent targeting construct without the aid of a capture device;
(e) removing tumor tissue identified by directly viewing the in vivo body cavity or organ; and
(f) allowing the therapeutic isotope molecule to remain in contact with residual tumor tissue not identified in step (e).

31. The method of claim 30, wherein the therapeutic isotope molecule is an electron emitter and a positron (+) beta emitter.

32. The method of claim 31, wherein the therapeutic isotope molecule is Samarium-153, Rhenium-188, or Copper-64.

33. The method of claim 30, wherein the compound is selected from the group consisting of a hormone, deoxyglucose, somatostatin, 1-amino-cyclobutane-1-carboxylic acid, methionine, a methionine derivative, histidine, or a combination of any two or more thereof.

34. The method of claim 33, wherein the compound is deoxyglucose.

35. The method of claim 30, wherein the light has at least one excitation wavelength in the range of 401 nm to 510 nm.

36. The method of claim 30, wherein the light is monochromatic, and wherein the excitation wavelength of the light is matched to an excitation wavelength of the fluorescent targeting construct.

37. The method of claim 30, wherein the fluorescent targeting construct is administered systemically.

38. The method of claim 30, wherein the diseased tissue is associated with a condition selected from the group consisting of tumors, pre-cancerous conditions, necrotic conditions, ischemic conditions, and inflammatory diseases.

* * * * *

UNITED STATES PATENT AND TRADEMARK OFFICE
CERTIFICATE OF CORRECTION

| | | |
|---|---|---|
| PATENT NO. | : 8,463,365 B2 | Page 1 of 1 |
| APPLICATION NO. | : 12/212582 | |
| DATED | : June 11, 2013 | |
| INVENTOR(S) | : George A. Luiken | |

It is certified that error appears in the above-identified patent and that said Letters Patent is hereby corrected as shown below:

In the Specifications

At Column 12, Line 13 (Approx.), please change "Chinacrine" to --Quinacrine--.

At Column 12, Line 31 (Approx.), please change "methylcourmarin" to --methylcoumarin--.

At Column 12, Line 40 (Approx.), please change "Nitrobenzoxadidole" to --Nitrobenzoxadiazole--.

At Column 19, Line 39, please change "proprionate;" to --propionate;--.

At Column 19, Line 40, please change "proprionamido" to --propionamido--.

In the Claims

At Column 27, Line 6, in Claim 9, please change "chromaggranin," to --chromogranin,--.

At Column 27, Lines 16-17, in Claim 12, please change "melanoma," to --malignant melanoma,--.

At Column 27, Line 25, in Claim 12, please change "or and" to --and--.

At Column 28, Line 17, in Claim 27, change "intercavitarily," to --intracavitarily,--.

Signed and Sealed this
Twenty-eighth Day of January, 2014

Michelle K. Lee
*Deputy Director of the United States Patent and Trademark Office*

SEQUENCE LISTING

<160> NUMBER OF SEQ ID NOS: 12

<210> SEQ ID NO 1
<211> LENGTH: 5
<212> TYPE: PRT
<213> ORGANISM: Artificial sequence
<220> FEATURE:
<223> OTHER INFORMATION: Synthetic construct

<400> SEQUENCE: 1

Gly Gly Gly Gly Ser
1               5

<210> SEQ ID NO 2
<211> LENGTH: 60
<212> TYPE: PRT
<213> ORGANISM: Artificial sequence
<220> FEATURE:
<223> OTHER INFORMATION: Synthetic construct

<400> SEQUENCE: 2

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser
    50                  55                  60

<210> SEQ ID NO 3
<211> LENGTH: 12
<212> TYPE: PRT
<213> ORGANISM: Artificial sequence
<220> FEATURE:
<223> OTHER INFORMATION: Synthetic construct

<400> SEQUENCE: 3

Gly Lys Ser Ser Gly Ser Gly Ser Glu Ser Lys Ser
1               5                   10

<210> SEQ ID NO 4

```
<211> LENGTH: 14
<212> TYPE: PRT
<213> ORGANISM: Artificial sequence
<220> FEATURE:
<223> OTHER INFORMATION: Synthetic construct

<400> SEQUENCE: 4

Gly Ser Thr Ser Gly Ser Gly Lys Ser Ser Glu Gly Lys Gly
1               5                   10

<210> SEQ ID NO 5
<211> LENGTH: 18
<212> TYPE: PRT
<213> ORGANISM: Artificial sequence
<220> FEATURE:
<223> OTHER INFORMATION: Synthetic construct

<400> SEQUENCE: 5

Gly Ser Thr Ser Gly Ser Gly Lys Ser Ser Glu Gly Ser Gly Ser Thr
1               5                   10                  15

Lys Gly

<210> SEQ ID NO 6
<211> LENGTH: 14
<212> TYPE: PRT
<213> ORGANISM: Artificial sequence
<220> FEATURE:
<223> OTHER INFORMATION: Synthetic construct

<400> SEQUENCE: 6

Gly Ser Thr Ser Gly Ser Gly Lys Ser Ser Glu Gly Lys Gly
1               5                   10

<210> SEQ ID NO 7
<211> LENGTH: 18
<212> TYPE: PRT
<213> ORGANISM: Artificial sequence
<220> FEATURE:
<223> OTHER INFORMATION: Synthetic construct

<400> SEQUENCE: 7

Gly Ser Thr Ser Gly Ser Gly Lys Pro Gly Ser Gly Glu Gly Ser Thr
1               5                   10                  15

Lys Gly

<210> SEQ ID NO 8
<211> LENGTH: 14
<212> TYPE: PRT
<213> ORGANISM: Artificial sequence
<220> FEATURE:
<223> OTHER INFORMATION: Synthetic construct

<400> SEQUENCE: 8

Glu Gly Lys Ser Ser Gly Ser Gly Ser Glu Ser Lys Glu Phe
1               5                   10

<210> SEQ ID NO 9
<211> LENGTH: 5
<212> TYPE: PRT
<213> ORGANISM: Artificial sequence
<220> FEATURE:
<223> OTHER INFORMATION: Synthetic construct

<400> SEQUENCE: 9

Ser Arg Ser Ser Gly
1               5
```

```
<210> SEQ ID NO 10
<211> LENGTH: 5
<212> TYPE: PRT
<213> ORGANISM: Artificial sequence
<220> FEATURE:
<223> OTHER INFORMATION: Synthetic construct

<400> SEQUENCE: 10

Ser Gly Ser Ser Cys
1               5

<210> SEQ ID NO 11
<211> LENGTH: 28
<212> TYPE: PRT
<213> ORGANISM: Artificial sequence
<220> FEATURE:
<223> OTHER INFORMATION: Synthetic construct

<400> SEQUENCE: 11

Ala Met Gly Arg Ser Gly Gly Gly Cys Ala Gly Asn Arg Val Gly Ser
1               5                   10                  15

Ser Leu Ser Cys Gly Gly Leu Asn Leu Gln Ala Met
            20                  25

<210> SEQ ID NO 12
<211> LENGTH: 60
<212> TYPE: PRT
<213> ORGANISM: Artificial sequence
<220> FEATURE:
<223> OTHER INFORMATION: Synthetic construct

<400> SEQUENCE: 12

Ala Met Gly Gly Gly Gly Ser Gly Gly Gly Gly Ser Gly Gly Gly Gly
1               5                   10                  15

Ser Gly Gly Gly Gly Ser Gly Gly Gly Gly Ser Gly Gly Gly Gly Ser
            20                  25                  30

Gly Gly Gly Gly Ser Gly Gly Gly Gly Ser Gly Gly Gly Gly Ser Gly
            35                  40                  45

Gly Gly Gly Ser Gly Gly Gly Gly Ser Gln Ala Met
        50                  55                  60
```